United States Patent [19]

Kweon

[11] Patent Number: 5,066,601

[45] Date of Patent: Nov. 19, 1991

[54] CANCER SCREENING METHOD UTILIZING A MODIFIED MILLON'S REAGENT

[75] Inventor: Jung M. Kweon, Seoul, Rep. of Korea

[73] Assignee: Sam I1 Pharmaceutical Manufacturing Co., Ltd., Rep. of Korea

[21] Appl. No.: 569,214

[22] Filed: Aug. 16, 1990

Related U.S. Application Data

[63] Continuation of Ser. No. 316,190, Feb. 27, 1989, abandoned.

[51] Int. Cl.$^5$ .............................................. G01N 33/48
[52] U.S. Cl. ........................................ 436/64; 436/63; 436/813
[58] Field of Search ............................ 436/64, 63, 813

[56] References Cited

U.S. PATENT DOCUMENTS

| | | | |
|---|---|---|---|
| 3,471,566 | 10/1969 | Roberts et al. | 568/449 |
| 3,615,857 | 10/1971 | Methlie | 429/52 |
| 3,966,493 | 6/1976 | Jung | 429/223 |
| 4,599,177 | 7/1986 | Hayashi et al. | 210/718 |

FOREIGN PATENT DOCUMENTS 8600575  5/1986  Rep. of Korea.

OTHER PUBLICATIONS

Bennington, "Saunder Dictionary & Encyclopedia of Laboratory Medicine and Technology" 1984, p. 979.
Weast et al., "CRC Handbook of Chemistry and Physics" 64th ed. 1984, p. D-138.

*Primary Examiner*—Robert J. Warden
*Assistant Examiner*—Lyle A. Alexander
*Attorney, Agent, or Firm*—Ladas & Parry

[57] ABSTRACT

There is disclosed a reagent composition for cancer diagnosis which is composed of a mercurous salt and a mercuric salt wherein the mercurous salt is $Hg_2(NO_3)_2$ and the mercuric salt is mercuric sulfate or, its hydrate or mercuric oxide.

10 Claims, No Drawings

CANCER SCREENING METHOD UTILIZING A MODIFIED MILLON'S REAGENT

This application is a continuation of application Ser. No. 07/316,190, filed Feb. 27, 1989, now abandoned.

BACKGROUND OF THE INVENTION

The present invention relates to the Millon's reagent which can be conveniently used in the screening diagnosis of cancers by detecting phenolic metabolites present in an increased amount in the urine of cancer patients.

Cancer is still an incurable, fatal disease which cannot be cured even by modern medicinal technology. Although its early discovery is absolutely necessary for treatment, most cancers are discovered only after they are either considerably developed or metastasized. Therefore, the opportunity for any early cure is often missed. This is due to low accuracy of conventional diagnostic methods and use of expensive equipments, such as NMRS, tomographs, etc., which can be a financial burden for patients. Furthermore, patients must be hospitalized to receive accurate assays, such as tissue assay. Because of those disadvantages, conventional diagnostic methods could not be utilized for early diagnosis of cancer.

Recently, a diagnostic method which utilizes tumor markers, such as CEA, α-Fetoprotein, etc., and monoclonal antibodies, has been introduced. However, its results vary greatly depending on the kind of cancer. Furthermore, under the said method, smokers and pregnant women were also diagnosed as positive. Because of such low accuracy and the economical disadvantage owing to its high cost, the above method is yet too premature to be utilized in early cancer screening diagnosis.

The present invention eliminates the disadvantages and problems caused by the Millon's reagent for cancer diagnosis of Korean Patent No. 21558, and provides a diagnosing reagent which can be utilized more conveniently and rapidly for cancer screening diagnosis than the conventional diagnosis methods.

A urine test is the most frequently used diagnostic technique for any diseases because collection of urine sample is very convenient. Various human metabolites are excreted through urine. It is a well known fact that excretion of a particular metabolite increases in a patient's urine according to the nature of the disease. In the case of cancer patients, it is supposed that phenolic metabolites from tyrosine, peptides and proteins having terminal tyrosine, which react with the Millon's reagent, are excreted excessively. Accordingly, it is very interesting to note that in the prior techniques, the urine of patient was allowed to react with the Millon's reagent to diagnose cancer.

Accordingly, in order to utilize the Millon's reagent clinically for the diagnosis of cancers, the present inventor, first, examined the Millon's reagent of Korean Patent No. 21558. As a result, the reagent made in a gel type by adding gelatine to a stock solution or a dilute solution of the solution prepared by dissolving mercuric sulfate in 15% sulfuric acid did not show any color reaction with tyrosine standard and even cancer patients' urine. However, the gel-type reagent, when made by adding gelatine to a dilute solution of the reagent prepared by using metallic mercury and concentrated nitric acid, showed the color reaction when added to cancer patients' urine. However, the color obtained was very weak and the reaction time was relatively long. Because of these shortcomings, it was very difficult to establish an objective criteria for distinguishing cancer patients from noncancer patients. Thus, this type of Millon's reagent was not suitable for the clinical assay.

The Millon's reagent is a non-specific confirming reagent used in the color confirmation tests to verify the presence of 3,5-unsubstituted p-hydroxyphenol derivatives, such as tyrosine. The Millon's reagent is used in the following two methods. One of the methods comprises dissolving metallic mercury in concentrated nitric acid or fuming nitric acid, and diluting the resulting solution with distilled water to a desired concentration for use. The other involves the addition of sulfuric acid solution of mercuric sulfate to the sample to be tested. The whole mixture is then heated in a water bath and finally either sodium nitrate or potassium nitrate is added to develop color. However, in the former case upon dissolving metallic mercury in concentrated nitric acid or fuming nitric acid large quantities of nitrogen dioxide gas are generated. This brings up the issues of environmental pollution and the safety of the operator handling the poisonous metallic mercury. In addition, if it is used as a reagent, formation of the mercuric salts and standardization of the acid concentration are very difficult. In the latter case, necessity of a heating operation makes the process complicated, and further, hydrolysis of proteins in the urine sample isolates substances interfering color developing process, such as tryptophan.

SUMMARY AND DETAILED DESCRIPTION OF THE INVENTION

In order to overcome such disadvantages, the present inventor took special notice of the fact that the reaction between the phenolic metabolites in the urines of cancer patients, non-cancer patients and normal people and the Millon's reagent has interrelationship with concentration, and preformed some examinations by varying the mixing ratio of the components of the Millon's reagent. As a result, the present inventor found that the most stable red to red-brown precipitates were obtained when a mixture of nitric acid solution of $Hg^+$ salt and sulfuric acid solution of $Hg^{+2}$ salt were added to the urine sample of cancer patient. This is the direct result of combining the advantages of two reagents. Although $Hg^+$ salt induces the color reaction with the phenolic metabolites, it is easily interfered by inorganic salts present in the sample. This is counter balanced by $Hg^{+2}$ salt which does not participate in the color reaction but does precipitate relatively easily with the inorganic salts thus removing those inorganic salts from the sample as precipitates. The color development with $Hg^+$ is therefore stimulated.

The present invention relates to a diagnosis of whether the affecting possibility of cancer is present, by observing the color of the precipitate which is formed by adding to the urine sample nitric acid solution of $Hg^+$ salt and the sulfuric acid solution of $Hg^{+2}$ salt at a certain ratio. Red or red-brown precipitates are observed in the urine of cancer patient while only white precipitates are observed in that of a healthy person.

In the composition of the present invention a mixture of nitric acid solution of $Hg^+$ salts and sulfuric acid solution of $Hg^{+2}$ salts in the ion concentration ratio of approximately 1 to 0.1-3 is preferably used. Nitric acid solution of $Hg^+$ salt is generally prepared by dissolving the concentration of $Hg_2(NO_3)_2$ or its hydrates to 1.25M with 1 to 2 moles of nitric acid the sulfuric acid solution of $Hg^{+2}$ salt is generally prepared by dissolving the concentration of $HgSO_4$ or $HgO$ to 0.25-1.25 mol with 5.6N sulfuric acid. In the composition of the present invention, since $Hg^{+2}$ ion does not participate in the color development reaction directly, only the amount necesary for removing the inorganic salts and other impurities that are present in the sample is sufficient. Accordingly, although no specific restrictions on the composition ratio between $Hg^+$ and $Hg^{+2}$ ions are imposed, the ratio of $Hg^{+2}$ ion to $Hg^{+2}$ ion is preferably 1 to 0.1-2, more preferably about 1 to 0.3-1.

If the ionic content of $Hg^{+2}$ ion is in excess, the color of the precipitate is weak. On the other hand, if $Hg^{+2}$ ion content is too small, the effect of the present invention decreases.

EXAMPLE 1

A solution prepared by dissolving 14 g of 1M $Hg_2(NO_3)_2.2H_2O$ in 20 ml of nitric acid and a solution prepared by dissolving 15 g of $HgSO_4$ in 100 ml of 6N sulfuric acid are mixed in the ratio of 1:2 by volume.

Separately, 5 ml of the urine sample to be tested are placed in a test tube. To this, 0.6 ml of the mixed reagent as prepared above is added. The whole mixture is throughly shaken and is allowed to stand for 1 to 2 minutes. Upon standing, red precipitates appear in cancer patients' urine while white precipitates are observed in the urine of non-cancer patients and healthy people.

EXAMPLE 2

A solution prepared by dissolving 14 g of $Hg_2(NO_3)_2.2H_2O$ in 20 ml of 1M nitric acid and a solution prepared by dissolving 10 g of HgO in 100 ml of sulfuric acid are mixed in the ratio of 1:2. Using this reagent, the test is carried out according to the procedure of Example 1.

The clinical effects obtained by the reagent of the present invention are as follows:

When the first morning urine samples are collected from 34 known cancer patients and 33 patients suffering from other diseases and tested according to the procedure of Example 1, high diagnosis rates with 85.3% sensitivity and 90.9% specificity were obtained as shown in Table 1.

TABLE 1

Test results of improved Millon's reagent

| Serial No. | Age | Sex | Diagnosis | Classification | Color reaction | Judgement |
|---|---|---|---|---|---|---|
| (1) | 43 | F | Breast cancer | Malignant | (+) | Positive |
| (2) | 49 | M | Laryngeal cancer | Malignant | (+) | Positive |
| (3) | 35 | F | Mammary tumor | Normal | (−) | Negative |
| (4) | 72 | M | Rectal leiomyosarcoma | Normal | (−) | Negative |
| (5) | 50 | M | Stomach cancer | Malignant | (+) | Positive |
| (6) | 61 | M | Pneumonia | Normal | (−) | Negative |
| (7) | 48 | F | GB Stone | Normal | (−) | Negative |
| (8) | 63 | F | Lung cancer | Malignant | (+) | Positive |
| (9) | 47 | M | Rectal cancer | Malignant | (+) | Positive |
| (10) | 57 | M | Bladder cancer | Malignant | (+) | Positive |
| (11) | 63 | M | Hepatoma | Malignant | (+) | Positive |
| (12) | 39 | M | Stomoch cancer | Malignant | (+) | Positive |
| (13) | 69 | F | Esophageal cancer | Malignant | (+) | Positive |
| (14) | 51 | M | Stomach cancer | Malignant | (+) | Positive |
| (15) | 53 | F | Rectal cancer | Malignant | (+) | Positive |
| (16) | 46 | M | Lung cancer | Malignant | (+) | Positive |
| (17) | 45 | M | Laryngeal cancer | Malignant | (+) | Positive |
| (18) | 60 | M | Biliary cancer | Malignant | (+) | Positive |
| (19) | 64 | M | Stomach cancer | Malignant | (+) | Positive |
| (20) | 17 | F | ALL | Malignant | (+) | Positive |
| (21) | 64 | F | Bronchogenic cancer | Malignant | (−) | False negative |
| (22) | 59 | M | Hepatoma | Malignant | (+) | Positive |
| (23) | 48 | M | Stomach cancer | Malignant | (+) | Positive |
| (24) | 49 | M | Duodenal cancer | Malignant | (+) | Positive |
| (25) | 36 | M | Diabetes | Normal | (−) | Negative |
| (26) | 36 | F | Cervical cancer | Malignant | (+) | Positive |
| (27) | 62 | M | Stomach cancer | Malignant | (+) | Positive |
| (28) | 44 | M | Rectal tumor | Normal | (−) | Negative |
| (29) | 30 | M | Pulmonary tuberculosis | Normal | (+) | False positive |
| (30) | 18 | M | Enchondroma | Benign | (−) | Negative |
| (31) | 21 | M | Pulmonary tuberculosis | Normal | (−) | Negative |
| (32) | 29 | F | Pregnancy | Normal | (−) | Negative |
| (33) | 53 | F | Hashimoto's disease | Normal | (−) | Negative |
| (34) | 63 | M | Bronchogenic cancer | Malignant | (+) | Positive |
| (35) | 39 | F | Uterine leiomyoma | Benign | (+) | False positive |
| (36) | 13 | M | Bone marrow cancer | Malignant | (+) | Positive |
| (37) | 67 | M | Colon cancer | Malignant | (+) | Positive |
| (38) | 70 | M | Bronchial cancer | Malignant | (+) | Positive |
| (39) | 52 | M | Peritoneal metastatic cancer | Malignant | (−) | False negative |
| (40) | 54 | F | Bronchitis | Normal | (−) | Negative |
| (41) | 43 | M | Pulmonary | Normal | (−) | Negative |

TABLE 1-continued

Test results of improved Millon's reagent

| Serial No. | Age | Sex | Diagnosis | Classification | Color reaction | Judgement |
|---|---|---|---|---|---|---|
| (42) | 70 | F | Lung cancer | Malignant | (+) | Positive |
| (43) | 64 | M | Gastritis | Normal | (−) | Negative |
| (44) | 80 | F | Stomach cancer | Malignant | (−) | False negative |
| (45) | 32 | M | Stomach cancer | Malignant | (+) | Positive |
| (46) | 57 | M | Stomach cancer | Malignant | (+) | Positive |
| (47) | 53 | F | Enterocleisis | Normal | (−) | Negative |
| (48) | 16 | F | Branchial cleft | Benign | (−) | Negative |
| (49) | 6 | F | Lipomatosis | Benign | (−) | Negative |
| (50) | 50 | F | Uterine cancer | Malignant | (−) | False negative |
| (51) | 65 | M | Gastritis | Normal | (−) | Negative |
| (52) | 64 | M | Stomach cancer | Malignant | (+) | Positive |
| (53) | 61 | F | Bronchitis | Normal | (−) | Negative |
| (54) | 64 | F | Renal cystoma | Benign | (+) | False positive |
| (55) | 26 | F | Colonitis | Normal | (−) | Negative |
| (56) | 37 | F | Placenta previa | Normal | (−) | Negative |
| (57) | 36 | F | Uterine leiomyoma | Normal | (−) | Negative |
| (58) | 55 | M | Pulmonary tuberculosis | Normal | (−) | Negative |
| (59) | 70 | M | Kidney syndrome | Normal | (−) | Negative |
| (60) | 43 | F | Uterine adenomyosis | Normal | (−) | Negative |
| (61) | 37 | M | Bronchiectasia | Normal | (−) | Negative |
| (62) | 26 | M | Anal fistula | Normal | (−) | Negative |
| (63) | 74 | M | Hemoptysis | Normal | (−) | Negative |
| (64) | 67 | F | Cholecystitis | Normal | (−) | Negative |
| (65) | 24 | M | Pulmonary tuberculosis | Normal | (−) | Negative |
| (66) | 70 | M | Stomach cancer | Malignant | (−) | False negative |
| (67) | 28 | F | Pulmonary tuberculosis | Normal | (−) | Negative |

Sensitivity = 29/34 = 85.3%
Specifity = 30/33 = 90.9%

In addition, when 118 working people, who were proven to be healthy at their regular check-ups, were tested, false positive rate was as low as 2.54%. Accordingly, the reagent of the present invention differentiates cancer patients from non-cancer patients and further has a very high utility in early screening diagnosis for cancer possibility because its urine test is quick and simple.

I claim:

1. A method for determining the presence or absence of phenolic metabolites in a urine sample of a patient in an amount greater than that present in the urine of a normal and non-cancerous patient comprising:
    providing a urine sample from the patient; and
    adding to the urine sample an amount of an aqueous solution comprising a water soluble mercuric salt and a water soluble mercurous salt in an amount sufficient to form a precipitate whereby the precipitate indicates the presence of phenolic metabolites in an amount greater than that present in the urine of a normal and non-cancerous patient where the precipitate includes a color and whereby the precipitate indicates the absence of phenolic metabolites in an amount greater than that present in the urine of a normal and non-cancerous patient where the precipitate is white.

2. The method of claim 1 wherein the aqueous solution comprises a water soluble mercuric salt and a water soluble mercurous salt wherein the ratio of mercuric ions to mercurous ions is: approximately 1 to 0.1–3, respectively.

3. The method of claim 1 wherein the water soluble mercuric salt is mercuric nitrate and the water soluble mercurous salt is mercurous sulfate.

4. The method of claim 1 wherein the color of the precipitate formed is selected from the group consisting of red or red-brown.

5. The method of claim 1 wherein the aqueous solution comprises a water soluble mercuric salt and a water soluble mercurous salt wherein the ratio of mercuric ions to mercurous ions is: 1 to 0.1–2.0, respectively.

6. The method of claim 5 wherein the aqueous solution comprises a water soluble mercuric salt and a water soluble mercurous salt wherein the ratio of mercuric ions to mercurous ions is: 1.0 to 0.3–1.0, respectively.

7. A method for determining the presence or absence of phenolic metabolites in a urine sample of a patient in an amount greater than that present in the urine of a normal and non-cancerous patient comprising:
    providing a urine sample from the patient; and
    adding to the urine sample an amount of an aqueous solution comprising mercuric nitrate and mercurous sulfate, wherein the ratio of mercuric ions to mercurous ions is: 1 to 0.1–3.0, respectively, in an amount sufficient to form a precipitate wherby the precipitate indicates the presence of phenolic metabolites in an amount greater than that present in the urine of a normal and non-cancerous patient where the precipitate includes a color and whereby the precipitate indicates the absence of phenolic metabolites in an amount greater than that present in the urine of a normal and non-cancerous patient where the precipitate is white.

8. The method of claim 7 wherein the ratio of mercuric ions to mercurous ions is: 1.0 to 0.10–2.0, respectively.

9. The method of claim 7 wherein the ratio of mercuric ions to mercurous ions is: 1.0 to 0.30–1.0, respectively.

10. The method of claim 7 wherein the color of the precipitate formed is selected from the group consisting of red or red-brown.

* * * * *